United States Patent
Zhou et al.

(10) Patent No.: US 10,065,901 B2
(45) Date of Patent: Sep. 4, 2018

(54) METHOD FOR PREPARING OPTICALLY ACTIVE CARBONYL COMPOUND

(71) Applicants: ZHEJIANG NHU COMPANY LTD., Shaoxing, Zhejiang Province (CN); SHANDONG NHU PHARMACEUTICAL CO., LTD., Weifang, Shandong Province (CN); ZHEJIANG UNIVERSITY, Hangzhou, Zhejiang Province (CN)

(72) Inventors: Yougui Zhou, Shaoxing (CN); Ming Yu, Shaoxing (CN); Jintao Yuan, Shaoxing (CN); Lei Zhao, Shaoxing (CN); Xiandong Zhu, Shaoxing (CN); Guangxiong Yu, Shaoxing (CN); Weiwei Su, Shaoxing (CN); Weikang Shao, Shaoxing (CN); Xingxing Shi, Shaoxing (CN); Yin Zhang, Shaoxing (CN); Ming Feng, Shaoxing (CN); Zhirong Chen, Hangzhou (CN); Haoran Li, Hangzhou (CN); Yuhong Zhang, Hangzhou (CN)

(73) Assignees: ZHEJIANG NHU COMPANY LTD., Shaoxing (CN); SHANDONG NHU PHARMACEUTICAL CO., LTD., Weifang (CN); ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 15/565,133

(22) PCT Filed: Nov. 29, 2016

(86) PCT No.: PCT/CN2016/107590
§ 371 (c)(1),
(2) Date: Oct. 6, 2017

(87) PCT Pub. No.: WO2017/114058
PCT Pub. Date: Jul. 6, 2017

(65) Prior Publication Data
US 2018/0105477 A1    Apr. 19, 2018

(30) Foreign Application Priority Data
Dec. 30, 2015 (CN) .......................... 2015 1 1025138

(51) Int. Cl.
| | | |
|---|---|---|
| *C07C 45/62* | (2006.01) | |
| *C07B 53/00* | (2006.01) | |
| *B01J 31/02* | (2006.01) | |
| *B01J 23/46* | (2006.01) | |
| *C07D 333/22* | (2006.01) | |
| *C07C 47/225* | (2006.01) | |
| *C07C 47/232* | (2006.01) | |
| *C07C 49/21* | (2006.01) | |
| *C07C 49/217* | (2006.01) | |
| *C07D 307/46* | (2006.01) | |
| *C07C 47/21* | (2006.01) | |

(52) U.S. Cl.
CPC .............. *C07B 53/00* (2013.01); *B01J 23/462* (2013.01); *B01J 23/464* (2013.01); *B01J 23/468* (2013.01); *B01J 31/0237* (2013.01); *C07C 45/62* (2013.01); *C07C 47/21* (2013.01); *C07C 47/225* (2013.01); *C07C 47/232* (2013.01); *C07C 49/21* (2013.01); *C07C 49/217* (2013.01); *C07D 307/46* (2013.01); *C07D 333/22* (2013.01)

(58) Field of Classification Search
CPC .......... C07C 45/62; C07C 47/21; C07B 53/00
See application file for complete search history.

(56) References Cited

U.S. PATENT DOCUMENTS 7,973,198 B2 * 7/2011 Schmidt-Leithoff ........................ C07B 53/00
568/388
2010/0324338 A1    12/2010 Maeda et al.

FOREIGN PATENT DOCUMENTS

| CN | 101675020 A | 3/2010 |
| CN | 103724170 A | 4/2014 |

OTHER PUBLICATIONS

Ouellet et al. Enantioselective Organocatalytic Hydride Reduction. J.A.C.S. vol. 127, 32-33. (Year: 2005).*
Mayer et al. Asymmetric Counteranion-Directed Catalysis. Angewandte Chemie International Ed. vol. 45, 4193-4195. (Year: 2006).*

* cited by examiner

*Primary Examiner* — Sikarl A Witherspoon
(74) *Attorney, Agent, or Firm* — Jiwen Chen

(57) ABSTRACT

The present invention discloses a method for preparing optically active carbonyl compound, comprising the following steps: under the catalysis of chiral amine salt and transition metal catalysts, with hydrogen and catalytic amount of dihydropyridine compound as hydrogen source, use α, β-unsaturated aldehydes or α, β-unsaturated troponoid compounds to conduct asymmetric catalytic reaction to obtain the optically active carbonyl compound. This method comes in moderate reaction condition, simple operation, and catalytic amount of dihydropyridine compounds usage, the target product is easy to be separated and purified from the reaction system, and the metal catalyst can be recycled, it is economical.

18 Claims, No Drawings

METHOD FOR PREPARING OPTICALLY ACTIVE CARBONYL COMPOUND

This is a U.S. national stage application of PCT Application No. PCT/CN2016/107590 under 35 U.S.C. 371, filed Nov. 29, 2016 in Chinese, claiming priority of Chinese Application No. 201511025138.8, filed Dec. 30, 2015, all of which are hereby incorporated by reference.

TECHNICAL FIELD

The present invention belongs to the technical field of asymmetric catalytic organic synthesis, specifically relates to a method that prepares optically active carbonyl compound through asymmetric catalytic hydrogenation using α, β-unsaturated aldehydes or α, β-unsaturated troponoid compounds as raw materials.

BACKGROUND ART

Optically active carbonyl compounds are important intermediates for synthesizing medicine, essences & flavors and pesticides. Whereas to conduct selective asymmetric hydrogenation reaction to the carbon-carbon double bond of α, β-unsaturated carbonyl compounds is an important approach for obtaining optically active carbonyl compounds. Chemists have developed various methods to conduct selective asymmetric hydrogenation reaction to the carbon-carbon double bond of α, β-unsaturated carbonyl compounds, such methods and their existing technical shortcomings are as follows:

(1) Homogeneous catalytic reactions adopting hydrogen as hydrogen source, since such methods hydrogenate carbon-carbon double bond with hydrogen using catalytic amount of homogeneous catalysts without adding reaction promoters, the catalysts can be recycled without producing a large amount of by-products. CN101675020 introduces a method for synthesizing optically active carbonyl compounds and the application of such method in preparing optically active (R)-citronellal. Such method uses the air-sensitive phosphine ligand chiraphos, and the reaction gas needs to use a certain proportion of CO and hydrogen, meanwhile, in order for the catalyst to be recycled, the catalysts need to be regenerated under certain conditions (*Asymmetric Catalysis on Industrial Scale*, ed. Blaser, H.-U., H.-J. Federsel. Wiley-VCH, Weinheim, Germany, 2010, pp. 187-205).

(2) CN103249484 describes a method that prepares optically active carbonyl compounds through heterogeneous metal catalytic reactions using hydrogen as hydrogen source, such method adopts catalysts such as metal catalyst, chiral cyclocompound and acid, and its reaction mechanism may involve double catalytic cycles (Chem. Commun., 2012, 48, 1772-1774). Although heterogeneous metal catalysts can be easily recycled from the reaction solution, non-ideal phenomena such as loss or inactivation may occur in the reaction solution.

(3) Asymmetric hydrogenation reaction that uses dihydropyridine compound as a negative hydrogen source to transfer hydrogen from α, β-unsaturated carbonyl compounds is another important method for preparing optically active carbonyl compounds. In 2005, MacMillan adopted this method and used stoichiometric dihydropyridine compounds to selectively transfer the negative hydrogen into the double bond of the unsaturated aldehyde, obtaining optically active β-substituted aldehyde (J. Am. Chem. Soc., 2005, 127, 32-33). In 2006, Benjamin List reported a method that prepares optically active carbonyl compound using chiral organic salt as catalyst and dihydropyridine compound as negative hydrogen source, which is primarily characterized in that: the chiral organic salt catalyst consists of chiral phosphate negative ion and achiral ammonium ion, and the dihydropyridine compound dosage is stoichiometric amount (Angew. Chem. Int. Ed. 2006, 45, 4193-4195). CN103724170 describes a method that asymmetrically synthesizes dextro-citronellal using citral as an initial material, such method also adopts stoichiometric dihydropyridine compound as a negative hydrogen source. The reason why stoichiometric dihydropyridine compound is required is that dihydropyridine compound will eventually become pyridine compound in the reaction system, therefore, dihydropyridine compound is non-recyclable hydrogen source in the reaction system, meanwhile, a large amount of dihydropyridine compound residues are left in the reaction system and are difficult to be separated from the target product, this is obviously against the economical rule.

Therefore, in order to overcome the technical problems existing in the above mentioned prior arts, a new method that is easier to operate, has moderate reaction condition and is more economical for preparing optically active carbonyl compound needs to be developed. Such a new method needs to satisfy the following characteristics: the catalysts can be easily recycled, and the original reaction activation level can be maintained; if a dihydropyridine compound is used as a negative hydrogen source, it shall be used as less as possible. Yonggui Zhou's research group (CN104710377) adopts biomimetic asymmetric catalysis technology to use the combination of hydrogen-metal Ru catalyst-catalytic amount of pyrroline[1,2-a]quinoxaline to asymmetrically hydrogenate the carbon-nitrogen double bond of unsaturated imine. Currently, this biomimetic asymmetric catalyst technology is primarily used for the asymmetric hydrogenation reaction of the carbon-nitrogen double bond of unsaturated imine, and no literature report on its application in asymmetric hydrogenation reaction of carbon-carbon double bond of unsaturated carbonyl compound yet.

SUMMARY OF THE INVENTION

The purpose of the present invention is to provide a method for preparing an optically active carbonyl compound. This method has moderate reaction condition, is easy to operate, and uses less amount of dihydropyridine compound, and uses recyclable catalysts.

A method for preparing an optically active carbonyl compound, comprising the following steps:

Under the catalysis of chiral amine salt and transition metal catalysts, with hydrogen and catalytic amount of dihydropyridine compound as hydrogen source, using α, β-unsaturated aldehydes or α, β-unsaturated troponoid compounds to conduct asymmetric catalytic reaction to obtain the optically active carbonyl compound;

The structures of the α, β-unsaturated aldehydes or α, β-unsaturated troponoid compounds are as shown in formula (I):

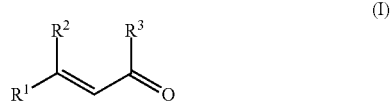

The structure of the optically active carbonyl compound is as shown in formula (II):

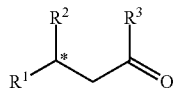

(II)

In formulas (I)-(II), $R^1$, $R^2$ and $R^3$ are independently selected from hydrogen, halogen, alkyl (including alkyl, alkenyl, aryl or aralkyl), heteroaryl, alkoxy or acylamino, wherein acylamino refers to substituent containing —CONH— or —NHCO—; $R^1$ and $R^2$ are different from each other, and $R^1$ and $R^2$ can form 5-15-member ring together with atoms connected with them, $R^1$ and $R^3$ can form 5-15-member ring together with atoms connected with them, $R^2$ and $R^3$ can also form 5-15-member ring together with atoms connected with them;

The structures of the chiral amine salt are as shown in formula (IV) or (V):

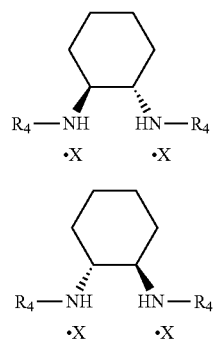

IV

V $R^4$ is selected from substituted or unsubstituted alkyl, the alkyl can be interrupted by one or more of the following radicals: O, —COO— and —CONH—;

Wherein the alkyl interrupted by O is alkyl containing ether or polyether, the alkyl interrupted by —COO— is alkyl containing ester or polyester, and the alkyl interrupted by —CONH— is alkyl containing acylamino or polyamide;

X means solidified acid;

* means asymmetric carbon atom.

Based on a series of research, the inventors discovered that by using specific chiral amine salt and metal as catalysts, and using hydrogen and catalytic amount of dihydropyridine compound as hydrogen source, reductive-hydrogenation reaction can be selectively conducted to the carbon-carbon double bond of α, β-unsaturated carbonyl compounds, preparing and & obtaining optically active carbonyl compounds, and the metal catalyst in the reaction system can be recycled through simple processing.

The specific reaction formula is as follows:

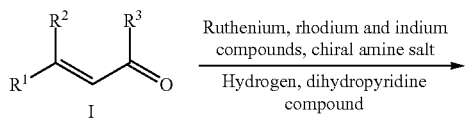

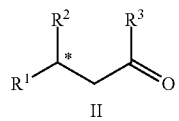

II

In the present invention, the alkyl, alkenyl, aryl, aralkyl, heteroaryl, alkoxy and acylamino herein are defined as follows:

Alkyl can be cyclo-alkyl or linear or branched alkyls containing 1 to 30 carbon atoms (1 to 20 carbon atoms as the optimum selection), and these alkyls can be alkyls that have substituents such as fluorine, chlorine, bromine, iodine, alkoxy, hydroxy and aryl, e.g., methyl, ethyl, n-propyl, isopropyl, normal-butyl, isobutyl, 2-butyl, tertiary butyl, n-amyl, 2-pentyl, 3-pentyl, tertiary pentyl, n-hexyl, cyclopropyl, cyclobutyl, cyclopentyl, cyclohexyl, heptyl, octyl, nonyl, decyl, hendecyl, dodecyl, tridecyl, myristyl, pentadecyl, hexadecyl, heptadecyl, octadecyl, nonadecyl, eicosyl, methyl-phenyl, 1-phenyl ethyl, and 2-phenyl ethyl.

Alkenyl can be cyclo-alkenyl or linear or branched alkenyl containing 2 to 20 carbon atoms, e.g., vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 1-cyclopentenyl, 3-cyclopentenyl, 1-cyclohexenyl, 3-cyclohexenyl, 4-methyl-3-pentenyl, 4,8-dimethyl-3,7-nonadienyl.

Aryl can be aryl containing 6 to 20 carbon atoms or aryl with substituent, e.g., phenyl, naphthyl, 4-methylphenyl, 2-methylphenyl, 3-methylphenyl, 4-methoxyphenyl, 2-methoxyphenyl, 3-methoxyphenyl, 4-tert-butylphenyl, 2-tert-butylphenyl, 3-tert-butylphenyl, 2,3-dimethoxyphenyl, 2,4-dimethoxyphenyl, 3,4-dimethoxyphenyl, 4-nitrobenzophenone, 4-chlorphenyl, 4-fluorophenyl, 4-bromophenyl, 4-iodophenyl, 4-trifluoromethylphenyl, 2-nitrobenzophenone, 2-chlorphenyl, 2-fluorophenyl, 2-bromophenyl, 2-iodophenyl, 2-trifluoromethylphenyl, 3-nitrobenzophenone, 3-chlorphenyl, 3-fluorophenyl, 3-bromophenyl, 3-iodophenyl, 3-trifluoromethylphenyl.

Heteroaryl can be aromatic heterocyclic aryls containing 3 to 9 carbon atoms, e.g., 2-furyl, 2-pyrryl, 2-thienyl, 2-pyridyl, 2-indolyl, 3-furyl, 3-pyrryl, 3-thienyl, 3-pyridyl, and 3-indolyl.

Alkoxy can be cyclo-alkoxy or linear or branched alkoxys containing 1 to 30 carbon atoms (1 to 20 carbon atoms as optimum selection), and these alkoxys can be alkoxys that have substituents such as fluorine, chlorine, bromine, iodine, hydroxy and aryl, e.g., methoxyl, ethyoxyl, n-propoxyethyl, isopropoxy, n-butoxy, isobutoxy, 2-butoxy, tert-butoxy, n-pentyloxy, 2-pentyloxy, 3-pentyloxy, tert-pentyloxy, n-hexyloxy, cyclopropoxy, cyclobutoxy, cyclopentyloxy, cyclohexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy, octadecyloxy, nonadecyloxy, eicosyloxy, phenylmethoxy, 1-phenylethoxy, and 2-phenylethoxy.

Acylamino is substituents containing —CONH— or —NHCO—, can be acylaminos containing 1 to 20 carbon atoms, e.g., formamido-, acetamido-, propionamido-, butyrylamino, valeramide-, hexanamide-, cyclopentylcarboxyl amine, cyclohexanecarboxamide, phenyl-formamido-, phenyl-acetamido- and naphthalene carboxamide amino.

In addition, in the catalytic system involved in the present invention, α, β-unsaturated carbonyl compounds are used as initial reaction materials, Z-configuration compound or E-configuration compound consisting of α double bond and β double bond can be used as reagents respectively, or mixture at certain proportion of Z-configuration compound and E-configuration compound can be used as reagents.

α, β-unsaturated carbonyl compounds as the reaction materials of this invention, their representative examples of can be given as compounds in the following formulas I-1 to I-30 (including without limitation), and the wave lines in the following structural formulas represent Z-configuration compound or E-configuration compound or mixture of the two configurations. Especially, this invention method is more suitable for optimum selection of neral (I-6a) or geranial (I-6b) or mixture of neral and geranial to prepare and obtain optically active citronellal (R-citronellal or (S)-citronellal), under this condition, the optical purity of citronellal is dependent on the purity of neral or geranial:

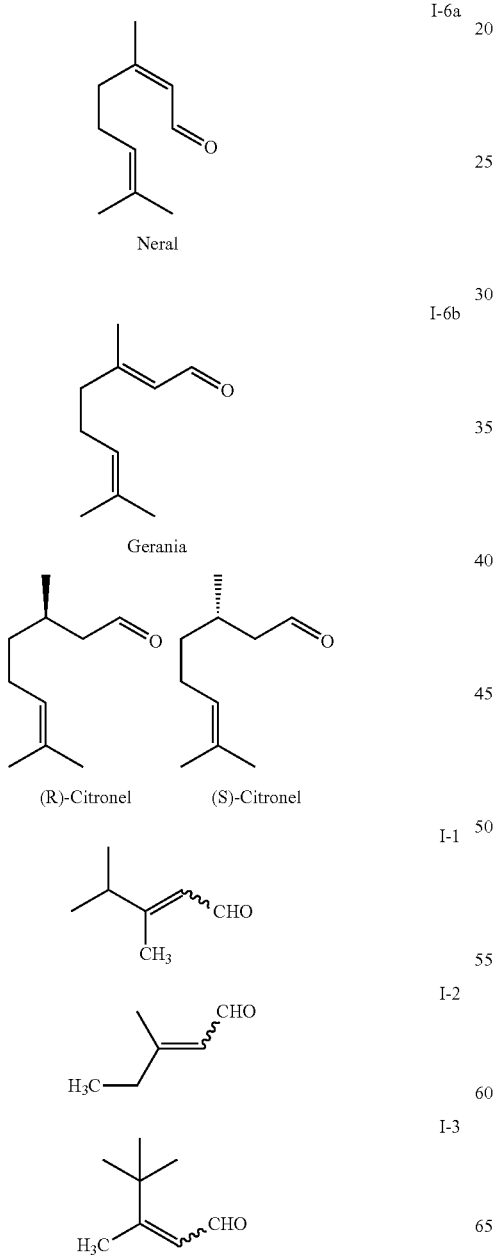

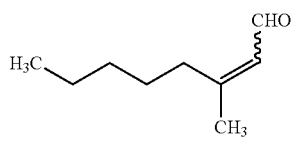

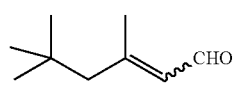

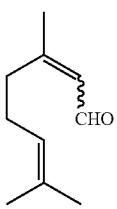

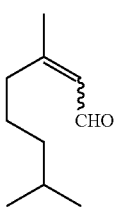

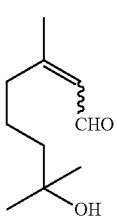

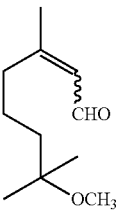

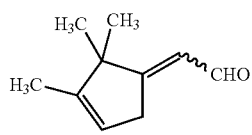

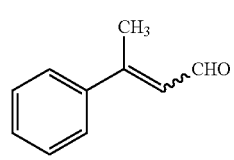

I-13 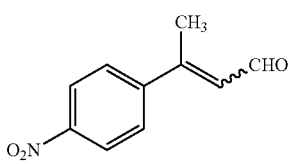

I-14 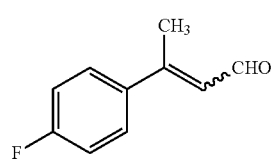

I-15 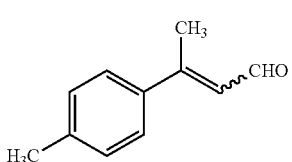

I-16 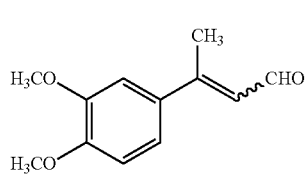

I-17 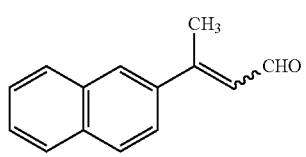

I-18 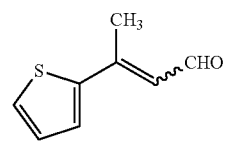

I-19 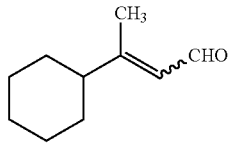

I-20 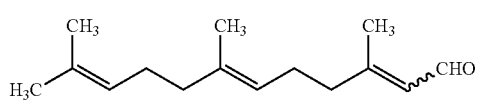

I-21 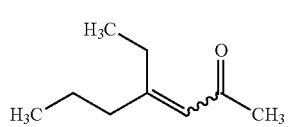

I-22 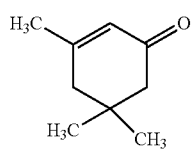

I-23 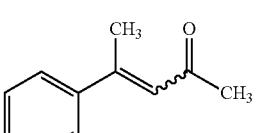

I-24 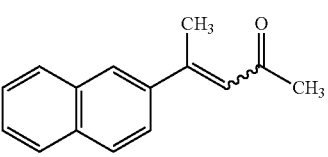

I-25 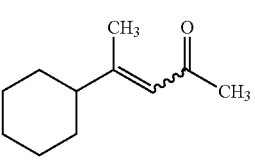

I-26 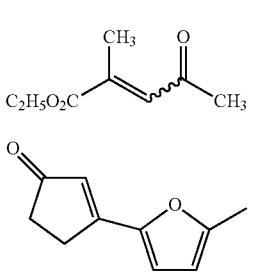

I-27 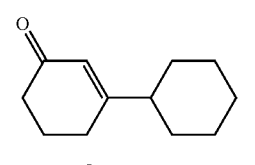

I-28 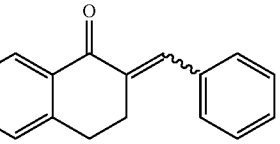

I-29

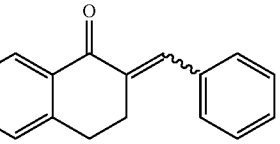

I-30

As preferred selection, the transition metal catalyst contains ruthenium compound, rhodium compound and indium compound, can be Ru(0), Ru(II), Ru(III), Ru(IV), Rh(0), Rh(I), Rh(III), Ir(0), Ir(I), Ir(III) and Ir(IV) compounds. As optimum selection, the transition metal catalysts include RuCl$_2$(PPh$_3$)$_3$, [Ru(p-cymene)Cl$_2$], [Ru(p-cymene)I$_2$]$_2$, RhCl$_3$, Rh$_2$(OAc)$_4$, Rh(CO)$_2$acac, Rh(cod)Cl$_2$, Rh$_4$(CO)$_{12}$, Ir$_4$(CO)$_{12}$, Ir(cod)Cl$_2$, [Ir(cod)OMe]$_2$, wherein "acac" is diacetone compound ligand, and "cod" is cyclooctadiene ligand.

As preferred selection, the solvent of the asymmetric catalytic hydrogenation reaction is methyl tertiary butyl ether, isopropyl ether, cyclopentylmethylether, ethylene glycol dimethyl ether, tetrahydrofuran, 2-methyltetrahydrofuran, methylbenzene, n-hexane, dichloromethane, 1,2-dichloroethane, methanol, ethanol, tertiary butanol, tert-amyl alcohol, isopropanol, water or mixture of these solvents.

Optimum selection is t-butylether, isopropyl ether, cyclopentylmethylether, ethylene glycol dimethyl ether, tetrahydrofuran, and 2-methyltetrahydrofuran or methylbenzene.

In the chiral amine salt of the present invention, as preferred selection, the $R^4$ is substituted or unsubstituted $C_1$~$C_{20}$ alkyls, such $C_1$~$C_{20}$alkyls contain cyclo-alkyl, linear alkyl or branched alkyl; the substituents on the alkyls include fluorine, chlorine, bromine, iodine, alkoxy, hydroxy and aryl; as further preferred selection, the $R^4$ is substituted or unsubstituted $C_1$~$C_{10}$ alkyls.

As additional preferred selection, the $R^4$ is methyl, ethyl, n-propyl, isopropyl, normal-butyl, isobutyl, 2-butyl, tertiary butyl, n-amyl, 2-pentyl, 3-pentyl, tertiary pentyl, n-hexyl, cyclopropyl, cyclobutyl, cyclopentyl, cyclohexyl, heptyl, octyl, nonyl, decyl, 1-indanyl, 2-indanyl, 1-1,2,3,4-tetralyl, 2-1,2,3,4-tetralyl; as further preferred selection, the $R^4$ is n-amyl, 2-pentyl, 3-pentyl, tertiary pentyl, n-hexyl, cyclopropyl, cyclobutyl, cyclopentyl, cyclohexyl, 1-indanyl, 2-indanyl, 1-1,2,3,4-tetralyl and 2-1,2,3,4-tetralyl.

As preferred selection, the X is selected from one of formic acid, acetic acid, propionic acid, trifluoroacetic acid, trichloroacetic acid, substituted or unsubstituted benzoic acid, mandelic acid, citric acid, substituted or unsubstituted 1,1'-binaphthyl-2,2'-diyl hydrogen-phosphate or from mixture of two or more of them. As further optimum selection, the x is trifluoroacetic acid, trichloroacetic acid, benzoic acid, mandelic acid, citric acid, 1,1'-binaphthyl-2,2'-diyl hydrogen-phosphate or from mixture of two or more of them.

The chiral amine

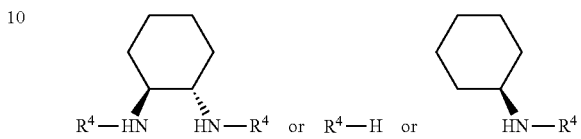

in the chiral amine salt of this invention can be prepared in reference to the methods disclosed by Chinese Chemical Letters, 2011, 22, 155-158 or Tetrahedron Letters, 2002, 43, 155-158, representative examples of optimum selection of compounds for the chiral amine are as follows (the difference between 31a~31n and 32a~32n is their different absolute configurations) (including without limitation):

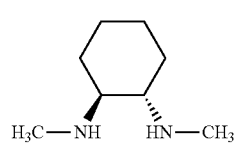

31a

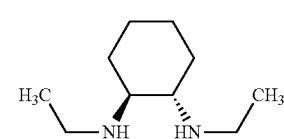

31b

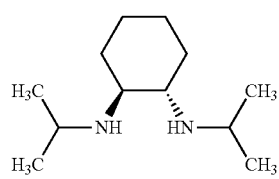

31c

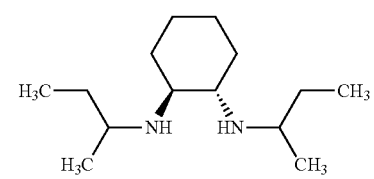

31d

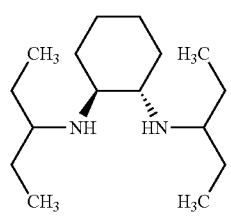

31e

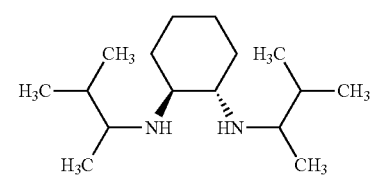

31f

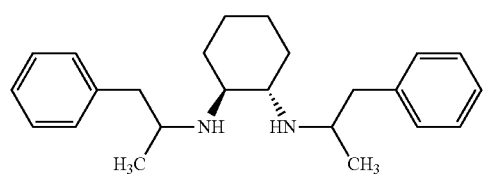

31g

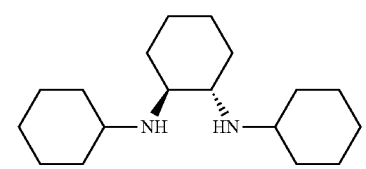

31h

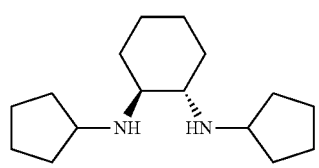

31i

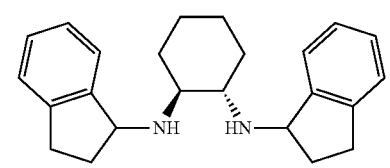

31j

-continued
| | |
|---|---|
| 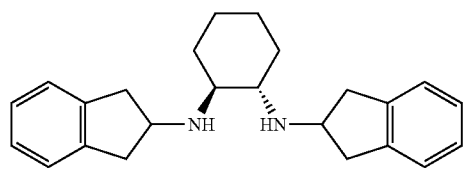 31k | 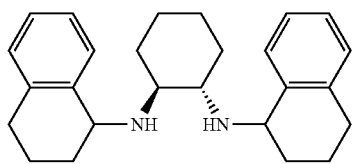 31l |
| 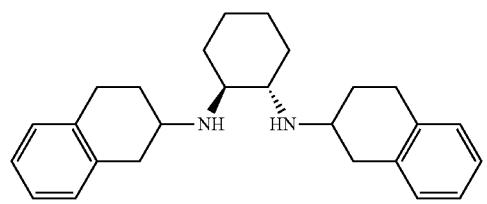 31m | |
| 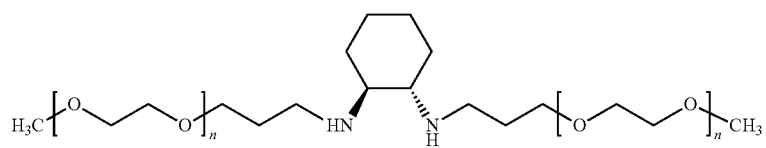 31n | |
| 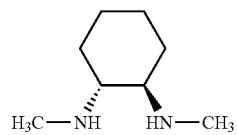 31a | 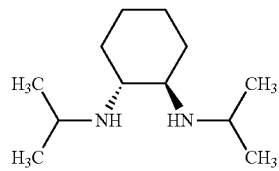 32b |
31a
32b
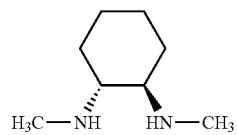
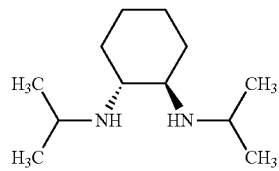
32c
32d
32e
32f
32g
32h
32i
32j
32k
32l
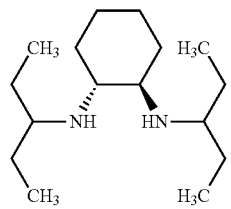
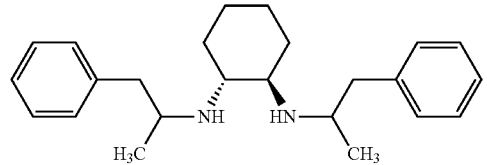
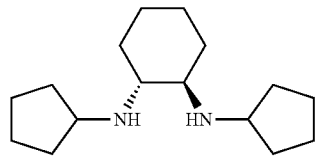
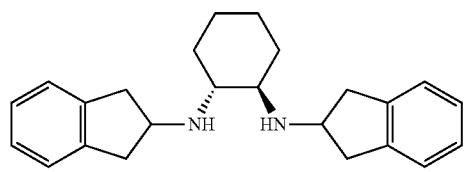
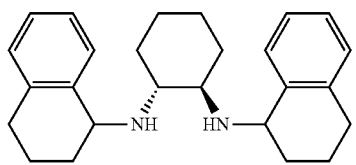

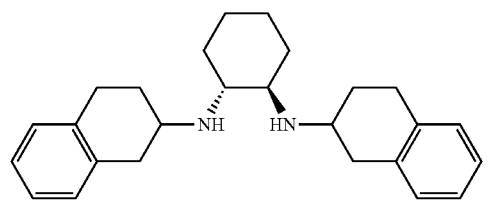

32m

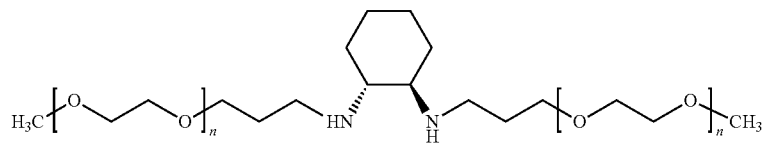

32n

As representative optimum selection examples, the following compounds can be selected for the dihydropyridine compounds involved in the present invention (including without limitation):

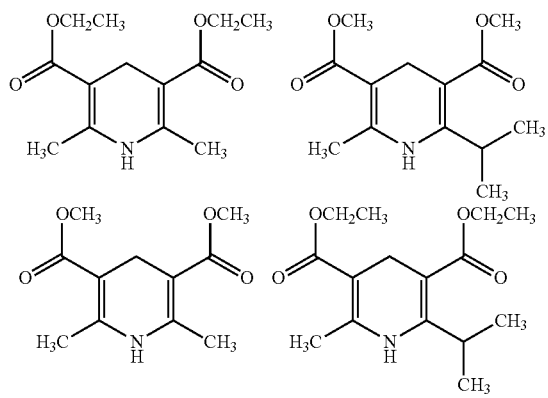

In the present invention, the solvent of the asymmetric catalytic hydrogenation reaction is methyl tertiary butyl ether, isopropyl ether, cyclopentylmethylether, ethylene glycol dimethyl ether, tetrahydrofuran, 2-methyltetrahydrofuran, methylbenzene, n-hexane, dichloromethane, 1,2-dichloroethane, methanol, ethanol, tertiary butanol, tert-amyl alcohol, isopropanol, water or mixture of these solvents, optimum selection is t-butylether, isopropyl ether, cyclopentylmethylether, ethylene glycol dimethyl ether, tetrahydrofuran, and 2-methyltetrahydrofuran or methylbenzene.

The temperature of the asymmetric hydrogenation reaction of the present invention is generally 20☐ to 120☐, optimum selection is 25☐ to 80☐.

The duration of the asymmetric hydrogenation reaction of the present invention is generally 10 to 72 hours.

The hydrogen reaction pressure in the asymmetric hydrogenation reaction of the present invention is 10 bar to 600 bar, optimum selection is 20 bar to 400 bar.

In the asymmetric hydrogenation reaction of the present invention, the dosage of the ruthenium compound, rhodium compound and indium compound to be used is 0.01 mol % to 20 mol % of α, β-unsaturated aldehydes or α, β-unsaturated troponoid reagents, optimum selection is 0.05 mol % to 10 mol %, especially 0.05 mol % to 5 mol %. After the reaction is completed, the solvent is removed through reduced pressure distillation and a product is obtained through rectification, n-heptane is added to the residual, filtered, leached with cold n-heptane and methyl alcohol sequentially, and finally vacuum-dried to realize metal catalyst recycling.

In the present invention, the dosage of the chiral amine salt to be used is 0.1 mol % to 20 mol % of α, β-unsaturated aldehydes or α, β-unsaturated troponoid reagents, optimum selection is 1 mol % to 10 mol %, especially 1.5 mol % to 5 mol %.

In the present invention, the dosage of the dihydropyridine compounds to be used is 0.2 mol % to 40 mol % of α, β-unsaturated aldehydes or α, β-unsaturated troponoid reagents, optimum selection is 2 mol % to 20 mol %, especially 3 mol % to 10 mol %.

Comparing to the prior art, the beneficial effects of the present invention are as follows:

(1) Moderate reaction condition, simple operation, catalytic amount dihydropyridine compounds usage, easy to separate and purify the target product from the reaction system;

(2) Recyclable metal catalyst, and economical.

SPECIFIC EMBODIMENTS OF THE INVENTION

Described below is the implementation process of the method for preparing optically active carbonyl compounds provided by the present invention as illustrated by specific embodiments, however, the present invention is not limited to these embodiments only, to technicians in this filed, any equivalent replacement and modification etc. shall fall within the scope of protection of the present invention.

Embodiments 1~16

Common method for preparing optically active citronellal (results listed in Table 1) are as follows: in the pressure reactor of 250 mL, under nitrogen protection condition, metal catalyst [Ru(p-cymene)I$_2$]$_2$ (4.8 mg, 0.005 mol), chiral amine salt (0.01 mol), dihydropyridine compound (0.05 mol), a mixture of geranial and neral (totally 15.2 g, 0.1 mol) and reactive solvent (110 mL) were added, the reaction mixture was stirred for 20 minutes under room temperature condition, then the system was heated up to 55° C., and the hydrogen in the reactor was replaced with 3 bar hydrogen, such hydrogen replacements were repeated, then hydrogen was quickly charged to the reactor to 100 bar pressure reaction, after 46 hours, after the material reaction is completed as proved by gas chromatography analysis, the reaction was stopped and cooled down to room temperature, the hydrogen in the reactor was slowly discharged, and the residual hydrogen in the reactor was replaced with nitrogen. The optical purity (i.e., enantiomeric excess value, ee value) of the product was analyzed by gas chromatography.

TABLE 1

Reaction results of embodiments 1~16

| Embodiment | Geranial: neral | Chiral amine salt | | Dihydropyridine compound | Solvent | Main configuration of citronellal | Yield (%) | ee (%) |
|---|---|---|---|---|---|---|---|---|
| | | Chiral amine | Acid | | | | | |
| 1 | 95:5 | 31a | $CF_3COOH$ | dimethyl 2-methyl-6-isopropyl-1,4-dihydropyridine-3,5-dicarboxylate | THF | S | 12 | 42 |
| 2 | 95:5 | 31b | $CF_3COOH$ | dimethyl 2,6-dimethyl-1,4-dihydropyridine-3,5-dicarboxylate | $CH_2Cl_2$ | S | 19 | 38 |
| 3 | 95:5 | 31c | $CF_3COOH$ | diethyl 2-methyl-6-isopropyl-1,4-dihydropyridine-3,5-dicarboxylate | THF:$CH_2Cl_2$ (1:5) | S | 81 | 18 |
| 4 | 95:5 | 31d | $CF_3COOH$ | diethyl 2,6-dimethyl-1,4-dihydropyridine-3,5-dicarboxylate | THF:$CH_2Cl_2$ (1:3) | S | 83 | 30 |
| 5 | 95:5 | 31e | $CF_3COOH$ | diethyl 2,6-dimethyl-1,4-dihydropyridine-3,5-dicarboxylate | THF:$CH_2Cl_2$ (1:3) | S | 82 | 35 |
| 6 | 95:5 | 31f | $CF_3COOH$ | diethyl 2,6-dimethyl-1,4-dihydropyridine-3,5-dicarboxylate | THF:$CH_2Cl_2$ (1:3) | S | 81 | 32 |
| 7 | 90:10 | 31g | $CF_3COOH$ | diethyl 2,6-dimethyl-1,4-dihydropyridine-3,5-dicarboxylate | THF:$CH_2Cl_2$ (1:3) | S | 89 | 55 |

TABLE 1-continued

Reaction results of embodiments 1~16

| Embodiment | Geranial:neral | Chiral amine salt | | Dihydropyridine compound | Solvent | Main configuration of citronellal | Yield (%) | ee (%) |
|---|---|---|---|---|---|---|---|---|
| | | Chiral amine | Acid | | | | | |
| 8 | 10:90 | 31j | CF$_3$COOH | diethyl 2,6-dimethyl-1,4-dihydropyridine-3,5-dicarboxylate | THF:CH$_2$Cl$_2$ (1:3) | R | 82 | 80 |
| 9 | 5:95 | 31j | CF$_3$COOH | diethyl 2,6-dimethyl-1,4-dihydropyridine-3,5-dicarboxylate | THF:CH$_2$Cl$_2$ (1:3) | R | 82 | 90 |
| 10 | 95:5 | 31h | CF$_3$COOH | diethyl 2,6-dimethyl-1,4-dihydropyridine-3,5-dicarboxylate | THF:CH$_2$Cl$_2$ (1:3) | S | 80 | 72 |
| 11 | 95:5 | 31i | CF$_3$COOH | diethyl 2,6-dimethyl-1,4-dihydropyridine-3,5-dicarboxylate | THF:CH$_2$Cl$_2$ (1:3) | S | 78 | 73 |
| 12 | 95:5 | 31j | CF$_3$COOH | diethyl 2,6-dimethyl-1,4-dihydropyridine-3,5-dicarboxylate | THF:CH$_2$Cl$_2$ (1:3) | S | 81 | 90 |
| 13 | 95:5 | 31k | CF$_3$COOH | diethyl 2,6-dimethyl-1,4-dihydropyridine-3,5-dicarboxylate | THF:CH$_2$Cl$_2$ (1:3) | S | 81 | 65 |
| 14 | 95:5 | 31l | CF$_3$COOH | diethyl 2,6-dimethyl-1,4-dihydropyridine-3,5-dicarboxylate | THF:CH$_2$Cl$_2$ (1:3) | S | 81 | 80 |
| 15 | 95:5 | 31m | CF$_3$COOH | diethyl 2,6-dimethyl-1,4-dihydropyridine-3,5-dicarboxylate | THF:CH$_2$Cl$_2$ (1:3) | S | 81 | 44 |

TABLE 1-continued

Reaction results of embodiments 1~16

| Embodiment | Geranial: neral | Chiral amine salt Chiral amine | Acid | Dihydropyridine compound | Solvent | Main configuration of citronellal | Yield (%) | ee (%) |
|---|---|---|---|---|---|---|---|---|
| 16 | 95:5 | 31n | $CF_3COOH$ | diethyl 2,6-dimethyl-1,4-dihydropyridine-3,5-dicarboxylate | $THF:CH_2Cl_2$ (1:3) | S | 72 | 21 |

Embodiments 17~20

Embodiments 17~20 were implemented in the same way as Embodiment 9, the difference was the different metal catalyst, and the results are listed in Table 2:

TABLE 2

Reaction results of embodiments 17~20

| Embodiment | Metal catalyst | Main configuration of citronellal | Yield (%) | ee (%) |
|---|---|---|---|---|
| 17 | [Ru(p-cymene)Cl$_2$] | R | 35 | 81 |
| 18 | Rh(CO)$_2$acac | R | 16 | 28 |
| 19 | [Ir(cod)OMe]$_2$ | R | 86 | 60 |
| 20 | RuCl$_2$(PPh$_3$)$_3$ | R | 5 | 0 |

Embodiments 21~26

Embodiments 21~26 were implemented in the same way as Embodiment 9, the difference was the different acid used by the chiral amine salt, and the results were listed in Table 3:

TABLE 3

Reaction results of embodiments 21~26

| Embodiment | Acid | Main configuration of citronellal | Yield (%) | ee (%) |
|---|---|---|---|---|
| 21 | HCl | R | 75 | 11 |
| 22 | Mandelic acid | R | 77 | 78 |
| 23 | Tartaric acid | R | 61 | 45 |
| 24 | Citric acid | R | 80 | 73 |

TABLE 3-continued

Reaction results of embodiments 21~26

| Embodiment | Acid | Main configuration of citronellal | Yield (%) | ee (%) |
|---|---|---|---|---|
| 25 | Parachlorobenzoic-acid | R | 80 | 65 |
| 26 | 1,1'-binaphthyl-2,2'-diyl hydrogen-phosphate | R | 75 | 66 |

Embodiments 27~30

Embodiments 27~30 were implemented in the same way as Embodiment 9, the difference was the dosage of the chiral amine salt, and the results were listed in Table 4:

TABLE 4

Reaction results of embodiments 27~30

| Embodiment | 32j, mol % | Trifluoroacetic acid, mol % | Main configuration of citronellal | Yield (%) | ee (%) |
|---|---|---|---|---|---|
| 27 | 1 | 1 | R | 63 | 88 |
| 28 | 5 | 5 | R | 72 | 90 |
| 29 | 15 | 15 | R | 82 | 90 |
| 30 | 20 | 20 | R | 82 | 90 |

Embodiments 31~34

Embodiments 31~34 were implemented in the same way as Embodiment 9, the difference was the different dosage of dihydropyridine compound, and the results were listed in Table 5:

TABLE 5

Reaction results of embodiments 31~34

| Embodiment | diethyl 2,6-dimethyl-1,4-dihydropyridine-3,5-dicarboxylate, mol % | Main configuration of citronellal | Yield (%) | ee (%) |
|---|---|---|---|---|
| 31 | 1 | R | 55 | 78 |
| 32 | 10 | R | 72 | 90 |

TABLE 5-continued

Reaction results of embodiments 31~34

| Embodiment | , mol % | Main configuration of citronellal | Yield (%) | ee (%) |
|---|---|---|---|---|
| 33 | 15 | R | 71 | 90 |
| 34 | 20 | R | 72 | 89 |

Embodiments 35~40

Embodiments 35~40 were implemented in the same way as Embodiment 9, the difference was the different metal catalyst dosage or different reaction hydrogen pressure, and the results are listed in Table 6:

TABLE 6

Reaction results of embodiments 35~40

| Embodiment | [Ru(p-cymene)I$_2$] mol % | Hydrogen pressure bar | Main configuration of citronellal | Yield (%) | ee (%) |
|---|---|---|---|---|---|
| 35 | 1.25 | 400 | R | 85 | 89 |
| 36 | 2.5 | 200 | R | 79 | 88 |
| 37 | 10 | 80 | R | 88 | 88 |
| 38 | 2.5 | 100 | R | 66 | 90 |
| 39 | 5 | 80 | R | 79 | 90 |
| 40 | 5 | 300 | R | 95 | 90 |

Embodiments 41~43

Embodiments 41~43 were embodiments of metal catalyst recycling experiments, the experimental conditions were the same as Embodiment 9.

The operation process was as follows: after the reaction of Embodiment 9 was stopped, the reaction was cooled down to room temperature, the hydrogen in the reactor was slowly discharged, and the residual hydrogen in the reactor was replaced with nitrogen. The optical purity (i.e., enantiomeric excess value, ee value) of the product was analyzed by gas chromatography. The solvent was removed through reduced pressure distillation and the product was obtained through rectification, n-heptane was added to the residual, filtered, leached with cold n-heptane and methyl alcohol sequentially, and finally vacuum-dried to obtain recycled catalyst. The recycling data are listed in Table 7:

TABLE 7

| Embodiment | Recycling times | Main configuration of citronellal | Yield (%) | ee (%) |
|---|---|---|---|---|
| 41 | 1st time | R | 82 | 90 |
| 42 | 2nd time | R | 81 | 90 |
| 43 | 3rd time | R | 82 | 88 |

It can be seen from Table 7 that the yield and ee value of the recycled catalyst through simple recycling processing have no obvious decrease.

The invention claimed is:

1. A method for preparing an optically active carbonyl compound, the method being characterized by and comprising the following steps:
   conducting asymmetric catalytic reaction to obtain the optically active carbonyl compound under catalysis of chiral amine salt and transition metal catalysts, with hydrogen and catalytic amount of dihydropyridine compound as hydrogen source, using α, β-unsaturated aldehydes or α, β-unsaturated troponoid compounds;
   wherein the structures of the α, β-unsaturated aldehydes or α, β-unsaturated troponoid compounds are as shown in formula (I):

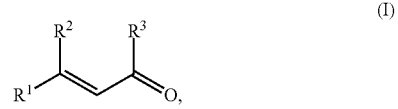

(I)

the structure of the optically active carbonyl compound is as shown in formula (II):

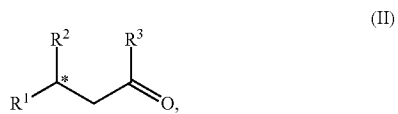

(II)

wherein in formulas (I)~(II), R$^1$, R$^2$ and R$^3$ are independently selected from hydrogen, halogen, alkyl, heteroaryl, alkoxy or acylamino, wherein acylamino refers to substituents containing —CONH— or —NHCO—, and R$^1$ is different from R$^2$;
the structures of the chiral amine salt are as shown in formula (IV) or (V):

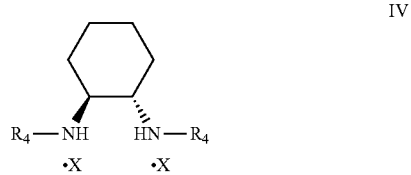

IV

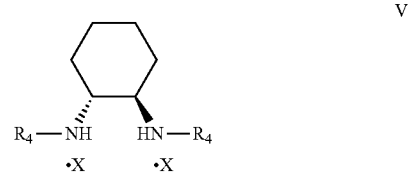

V

R⁴ is selected from substituted or unsubstituted alkyl, the alkyl refers to alkyl containing ether or polyether, alkyl containing ester or polyester, alkyl containing acylamino or polyamide, or polymer chain alkyl containing mixture of ether, ester and acylamino, wherein acylamino refers to substituents containing —CONH— or —NHCO—;

X means solidified acid;

* means asymmetric carbon atom.

2. The method for preparing an optically active carbonyl compound according to claim 1, which is characterized in that: in the R¹, R² and R³, alkyl is alkyl containing 1 to 30 carbon atoms;

heteroaryl is aromatic heterocyclic aryls containing 3 to 9 carbon atoms;

alkoxy is cyclo-alkoxy or linear or branched alkoxys containing 1 to 30 carbon atoms, and these alkoxys can be substituted by fluorine, chlorine, bromine, iodine, hydroxy or aryl;

acylaminos are acylaminos containing 1 to 20 carbon atoms.

3. The method for preparing an optically active carbonyl compound according to claim 2, which is characterized in that: the heteroaryl is: 2-furyl, 2-pyrryl, 2-thienyl, 2-pyridyl, 2-indolyl, 3-furyl, 3-pyrryl, 3-thienyl, 3-pyridyl, or 3-indolyl;

the alkoxies are: methoxyl, ethyoxyl, n-propoxyethyl, isopropoxy, n-butoxy, isobutoxy, 2-butoxy, tert-butoxy, n-pentyloxy, 2-pentyloxy, 2-pentyloxy, tert-pentyloxy, n-hexyloxy, cyclopropoxy, cyclobutoxy, cyclopentyloxy, cyclohexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy, octadecyloxy, nonadecyloxy, eicosyloxy, phenylmethoxy, 1-phenylethoxy, or 2-phenylethoxy;

the acylaminos can be: formamido-, acetamido-, propionamido-, butyrylamino, valeramide-amino, hexanamide-amino, cyclopentylcarboxyl amine, cyclohexanamide-amino, or phenyl-formamido-, phenylacetamido- or naphthalene carboxamide amino.

4. The method for preparing an optically active carbonyl compound according to claim 1, which is characterized in that: the R¹ and R² form 5-15-member ring together with atoms connected with them, or R¹ and R³ form 5-15-member ring together with atoms connected with them, or R² and R³ form 5-15-member ring together with atoms connected with them.

5. The method for preparing an optically active carbonyl compound according to claim 1, which is characterized in that: the compound (I) is selected from compounds with the following structures:

I-1

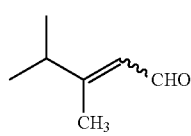

I-2

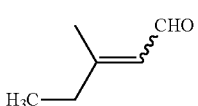

I-3

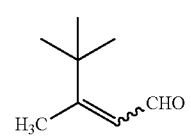

I-4

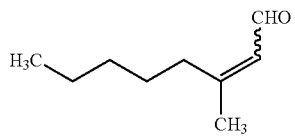

I-5

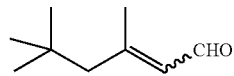

I-6

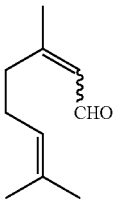

I-7

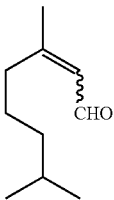

I-8

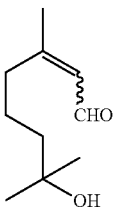

I-9

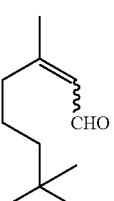

I-10

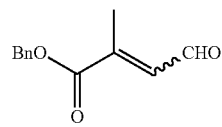

I-11

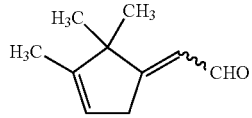

I-12

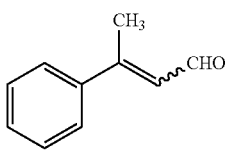

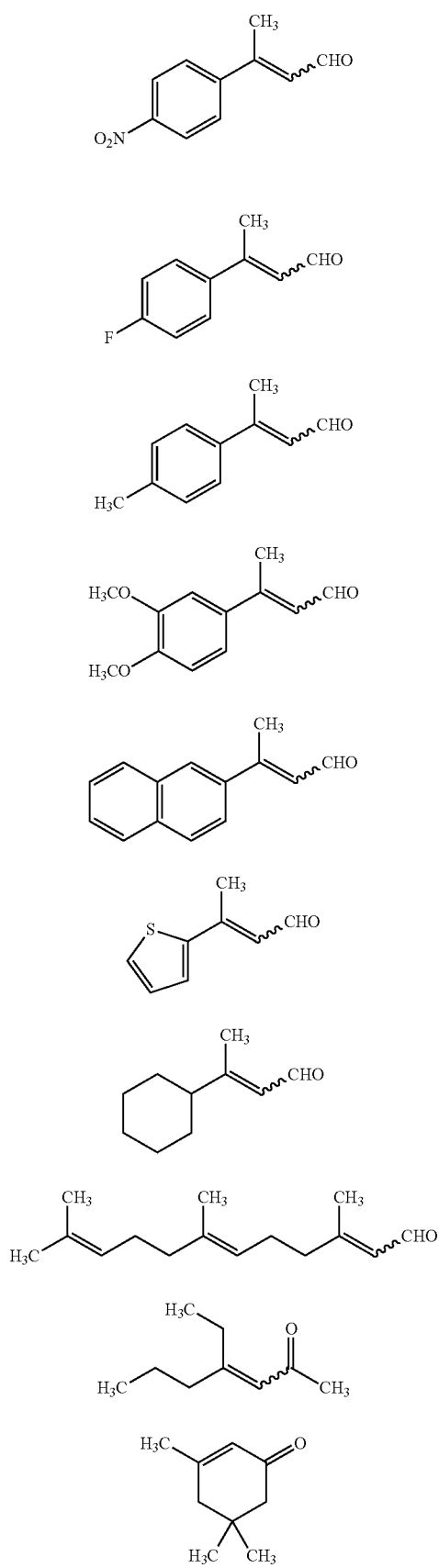
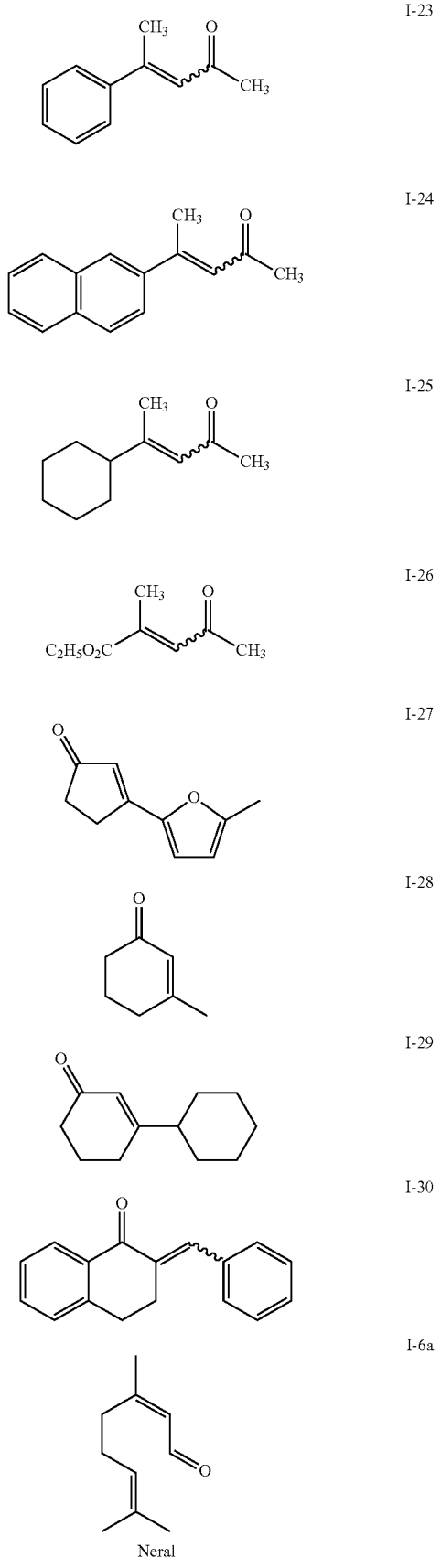

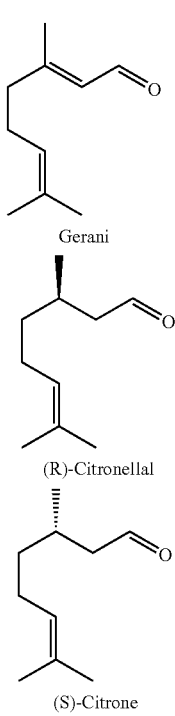

Gerani (R)-Citronellal (S)-Citrone

6. The method for preparing an optically active carbonyl compound according to claim 1, which is characterized in that: the $R^4$ is substituted or unsubstituted $C_1~C_{20}$ alkyls;
the substituents on the $C_1~C_{20}$ alkyls include fluorine, chlorine, bromine, iodine, alkoxy, hydroxy or aryl.

7. The method for preparing an optically active carbonyl compound according to claim 6, which is characterized in that: the $R^4$ is methyl, ethyl, n-propyl, isopropyl, normal-butyl, isobutyl, 2-butyl, tertiary butyl, n-amyl, 2-pentyl, 3-pentyl, tertiary pentyl, n-hexyl, cyclopropyl, cyclobutyl, cyclopentyl, cyclohexyl, heptyl, octyl, nonyl, decyl, 1-indanyl, 2-indanyl, 1-1,2,3,4-tetralyl, or 2-1,2,3,4-tetralyl.

8. The method for preparing an optically active carbonyl compound according to claim 1, which is characterized in that: the alkyl represented by the $R^4$ is interrupted by one or more of the following radicals: O, —COO— and —CONH—;
wherein the alkyl interrupted by O is alkyl containing ether or polyether, the alkyl interrupted by —COO— is alkyl containing ester or polyester, and the alkyl interrupted by —CONH— is alkyl containing acylamino or polyamide.

9. The method for preparing an optically active carbonyl compound according to claim 1, which is characterized in that: the X is selected from one of formic acid, acetic acid, propionic acid, trifluoroacetic acid, trichloroacetic acid, substituted or unsubstituted benzoic acid, mandelic acid, citric acid, substituted or unsubstituted 1,1'-binaphthyl-2,2'-diyl hydrogen-phosphate or from mixture of two or more of them.

10. The method for preparing an optically active carbonyl compound according to claim 1, which is characterized in that: the transition metal catalyst contains ruthenium compound, rhodium compound and indium compound.

11. The method for preparing an optically active carbonyl compound according to claim 1, which is characterized in that: the transition metal catalyst is selected from $RuCl_2(PPh_3)_3$, [Ru(p-cymene)$Cl_2$]$_2$, [Ru(p-cymene)$I_2$]$_2$, $RhCl_3$, $Rh_2(OAc)_4$, $Rh(CO)_2$acac, $Rh(cod)Cl_2$, $Rh_4(CO)_{12}$, $Ir_4(CO)_{12}$, $Ir(cod)Cl_2$ or [Ir(cod)OMe]$_2$.

12. The method for preparing an optically active carbonyl compound according to claim 1, which is characterized in that: the dihydropyridine compound is selected from one of the following compounds:

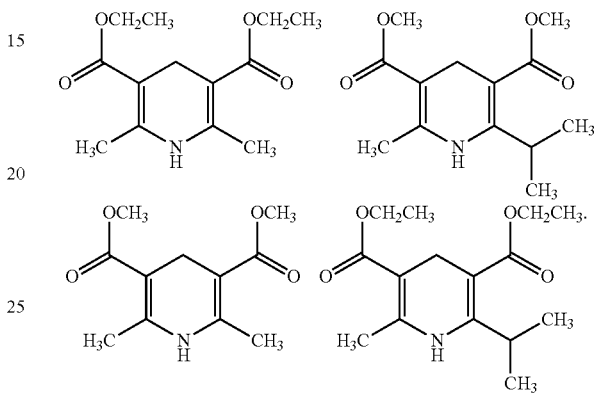

13. The method for preparing an optically active carbonyl compound according to claim 1, which is characterized in that: the solvent of the asymmetric catalytic hydrogenation reaction is methyl tertiary butyl ether, isopropyl ether, cyclopentylmethylether, ethylene glycol dimethyl ether, tetrahydrofuran, 2-methyltetrahydrofuran, methylbenzene, n-hexane, dichloromethane, 1,2-dichloroethane, methanol, ethanol, tertiary butanol, tert-amyl alcohol, isopropanol, water or mixture of these solvents.

14. The method for preparing an optically active carbonyl compound according to claim 1, which is characterized in that: the temperature of the asymmetric catalytic hydrogenation reaction is 20~120° C.

15. The method for preparing an optically active carbonyl compound according to claim 1, which is characterized in that: the hydrogen pressure in the asymmetric catalytic hydrogenation reaction is 10~600 bar.

16. The method for preparing an optically active carbonyl compound according to claim 1, which is characterized in that: the dosage of the transition metal catalyst is 0.01 mol % to 20 mol % of α, β-unsaturated aldehydes or α, β-unsaturated troponoid reagents.

17. The method for preparing an optically active carbonyl compound according to claim 1, which is characterized in that: the dosage of the chiral amine salt is 0.1 mol % to 20 mol % of α, β-unsaturated aldehydes or α, β-unsaturated troponoid reagents.

18. The method for preparing an optically active carbonyl compound according to claim 1, which is characterized in that: the dosage of the dihydropyridine compound is 0.2 mol % to 40 mol % of α, β-unsaturated aldehydes or α, β-unsaturated troponoid reagents.

* * * * *